United States Patent [19]

Ippisch

[11] Patent Number: 5,645,206

[45] Date of Patent: Jul. 8, 1997

[54] AUTOMATED DENTAL FLOSS DISPENSING APPARATUS

[76] Inventor: Kevin Ippisch, 427 Rosedale Ct., Capitola, Calif. 95010

[21] Appl. No.: 714,621

[22] Filed: Sep. 16, 1996

Related U.S. Application Data

[63] Continuation of Ser. No. 298,791, Aug. 31, 1994, abandoned, which is a continuation-in-part of Ser. No. 27,339, Mar. 8, 1993, abandoned.

[51] Int. Cl.$^6$ .......................... B65H 75/00; A61C 15/04
[52] U.S. Cl. .................. 225/10; 132/322; 83/649
[58] Field of Search ................... 225/10, 11, 34, 225/14, 15; 132/322, 323, 324, 325; 83/649

[56] References Cited

U.S. PATENT DOCUMENTS

| | | | |
|---|---|---|---|
| Re. 2,758 | 2/1867 | Postolowski | 83/241 X |
| 2,732,271 | 1/1956 | Hanson | 225/10 X |
| 3,046,882 | 7/1962 | Aubrey et al. | 225/11 X |
| 3,177,750 | 4/1965 | Amemiya | 83/241 X |
| 3,202,028 | 8/1965 | Rabelow et al. | 83/241 |
| 3,237,595 | 3/1966 | Kilham | 225/10 X |
| 3,246,797 | 4/1966 | Hoenisch | 225/10 X |
| 3,374,698 | 3/1968 | Sleeper | 83/241 X |
| 3,667,483 | 6/1972 | McCabe | 132/322 |
| 3,690,531 | 9/1972 | Tanigami | 225/10 X |
| 3,730,409 | 5/1973 | Ratti | 225/10 X |
| 3,784,073 | 1/1974 | Faggetter | 83/208 X |
| 3,847,167 | 11/1974 | Brien | 132/322 |
| 3,949,918 | 4/1976 | Golner et al. | 225/11 |
| 3,998,308 | 12/1976 | Yeakley | 225/10 X |
| 4,235,253 | 11/1980 | Moore | 132/322 |
| 4,245,658 | 1/1981 | Lecouturier | 132/322 |
| 4,307,740 | 12/1981 | Florindez et al. | 132/322 |
| 4,326,549 | 4/1982 | Hinding | 132/322 |
| 4,458,702 | 7/1984 | Grollimund | 132/322 |
| 4,524,657 | 6/1985 | Griffith | 83/208 X |
| 4,527,722 | 7/1985 | Strachan | 225/34 X |
| 4,586,521 | 5/1986 | Urso | 132/322 |
| 4,605,025 | 8/1986 | McSpadden | 132/322 |
| 4,638,696 | 1/1987 | Urwyler | 83/261 |
| 4,712,460 | 12/1987 | Allen et al. | 83/208 |
| 5,016,660 | 5/1991 | Boggs | 132/322 |
| 5,048,737 | 9/1991 | Sueda et al. | 225/11 |
| 5,069,233 | 12/1991 | Ritter | 132/322 |
| 5,170,809 | 12/1992 | Imai et al. | 132/322 |
| 5,176,157 | 1/1993 | Mazza | 132/322 |
| 5,186,191 | 2/1993 | Loubier | 132/324 X |
| 5,188,133 | 2/1993 | Romanus | 132/325 |
| 5,207,773 | 5/1993 | Henderson | 132/323 X |
| 5,217,031 | 6/1993 | Santoro | 132/324 X |
| 5,224,500 | 7/1993 | Stella | 132/322 |

*Primary Examiner*—Rinaldi I. Rada
*Assistant Examiner*—Elizabeth Stanley

[57] ABSTRACT

An automated dental floss dispensing apparatus for dispensing waxed or unwaxed floss, the apparatus having a dispenser housing including a spool receptacle for retaining a spool of floss. The spool receptacle has a conically shaped discharge aperture with inwardly slanting walls for feeding and guiding the dental floss and the dispenser housing includes a dispensing aperture for dispensing the floss. A cutter is disposed adjacent to the dispensing aperture for cutting a selected length of floss. A battery driven motor is operably coupled to a first and a second circuit for control of motor operating speed and for control of the length of floss to be dispensed by selective activation and deactivation of the motor. A control panel and a start button are included in a wall of the dispenser housing and the dispenser housing is preferably configured as two units which may be separated from one another, with one of the units having a removeable front panel to facilitate access inside the dispenser housing. The walls of the dispenser housing may be provided with one or more slots to receive corresponding projections on different units to allow combining two or more dispensers together.

16 Claims, 3 Drawing Sheets

AUTOMATED DENTAL FLOSS DISPENSING APPARATUS

RELATED APPLICATIONS

This is a continuation of Ser. No. 08/298,791, filed Aug. 31, 1994, now abandoned, which is a continuation-in-part of Ser. No. 08/027,339 filed Mar. 8, 1993, now abandoned.

BACKGROUND OF THE INVENTION

1. Field of Invention

This invention relates to elongated material dispensing apparatuses, and more particularly to dispensing apparatuses for dental floss, sulcular cord, or the like.

2. Description of Prior Art

In the practice of medicinal and dental rots a wide variety of flexible elongated materials such as dental floss, sulcular cord, tape, drug-containing tapes, and other dispensing strip-like materials are commonly used. Of concern to both the practitioner and the patient are sterile handling procedures, accuracy, and efficiency in the dispensing of such materials. This is especially true in contemporary practice with contagious diseases such as AIDS and hepatitis transmitted by both parenteral and nonparenteral routes.

Heretofore a wide variety of dispensing apparatuses have been proposed and implemented. None, however, are known to applicant in which a measured quantity of floss, sulcular cord, or the like, can be automatically dispensed in a controlled and sanitary manner.

One of the most significant limitations with all prior art dispensing apparatuses is the inability to dispense, a selective amount of dental floss, whether waxed or unwaxed, tape, or strip-like material, in a controlled and sterile fashion. Moreover, the unique properties of floss and sulcular cord make them particularly difficult to dispense. These properties included: 1. A limpness which causes them to misdirect in any direction and which causes them to clump or coil. 2. Their tendency to wrap around rollers (especially waxed floss). The prior art devices are complex, cumbersome and unable to dispense floss and sulcular cord since they provide no means of guiding and controlling the floss and sulcular cord for dispensing. They also have inherent features which contribute to the wrapping and coiling effects. Such limitations have undoubtedly been a reason these prior art dispensers have not received any acceptance for the dispensing of floss and sulcular cord. In fact, for example, it is unknown to provide a dental floss dispenser where controlled lengths of floss can be accurately, sterilely, and selectively dispensed.

Accordingly, it is the primary object of this invention to provide an improved dispensing apparatus for dispensing dental floss, or the like, for controlled, sterile, and selective dispensation, regardless of the amount of material remaining on the spool being dispensed, or whether the material is waxed or unwaxed, or otherwise treated.

Additional objects and advantages of the invention will be set forth in the description which follows, and in part will be obvious from the description, or may be learned by practice of the invention. The objects and advantages of the invention may be obtained by means of the instrumentalities and combinations particularly pointed out in the appended claims.

SUMMARY OF THE INVENTION

To achieve the foregoing objects, and in accordance with the purposes of the invention as embodied and broadly described herein, an automated dental floss dispensing apparatus for dispensing dental floss or sulcular cord is provided, comprising: a portable dispenser housing having a dispensing receptacle with a cortically shaped discharge aperture allowing for dental floss to be fed and guided through said conically shaped discharge aperture; said dispenser housing includes a dispensing aperture with a cutter disposed proximate to said dispensing aperture for cutting a selected length of material; said cutter being positioned adjacent to and protruding into said dispensing aperture allowing for guidance, positioning, and cutting of said floss; drive means operably mounted within said dispenser housing; a pair of rollers operably secured within said dispenser housing and positioned above said cortically shaped discharge aperture and below said dispensing aperture, said pair of rollers being adapted to receive and engage material to be dispensed, said pair of rollers are operably coupled to said drive means; and control means for controlling and actuating said drive means for automatically measuring a selected length of material to be dispensed.

The drive means of the dispensing apparatus preferably comprises a battery driven motor and the dispenser housing includes a control panel operably coupled to said control means for controlling and activating said drive means. The control means preferably comprise a first circuit operably coupled to said motor to control the motor operating speed, and a second circuit operably coupled to said motor to control a length of floss to be dispensed by limiting the duration of operation of said motor.

The dispenser housing is preferably configured as two units which are detachable from one another to facilitate loading a spool or roll of material to be dispensed in the dispensing receptacle. Means are provided to couple two or more dispensing units together and preferably comprise one or more receiving slots in a wall of said dispenser housing adapted to mate with one or more projections on a corresponding wall of a different dispensing unit.

In accordance with the purposes of the invention, there is also provided an automated dental floss dispensing apparatus for dispensing waxed or unwaxed dental floss from a source of material, comprising: a dispenser housing having a spool receptacle for retaining a spool of floss, said spool receptacle having a conically shaped discharge aperture having conically shaped walls therein allowing said dental floss to be fed and guided through said conically shaped discharge aperture, said dispenser housing includes a dispensing aperture for dispensing said floss; a cutter disposed adjacent to said dispensing aperture, said cutter being positioned adjacent to and protruding into said dispensing aperture allowing for guidance, positioning, and cutting of said floss; drive means operably mounted within said dispenser housing; a pair of rollers mounted within said dispenser housing directly above said conically shaped discharge aperture and directly below the dispensing aperture, said pair of rollers being adapted to receive and engage said floss from said spool, said pair of rollers being operably coupled to said drive means; and control means for controlling and actuating said drive means for automatically measuring a selective length of the floss to be dispensed.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

DETAILED DESCRIPTION OF THE PREFERRED EMBODIMENT

Reference will now be made in detail to the present preferred embodiments of the invention as illustrated in the accompanying drawings.

In accordance with the present invention, there is provided an automated dispensing apparatus for dental floss and sulcular cord, comprising: a dispenser housing having a spool receptacle for retaining a spool of floss, said spool receptacle having a cortically shaped discharge aperture with inwardly slanting walls; said dispenser housing includes a dispensing aperture for dispensing said floss; a cutter disposed adjacent to said dispensing aperture, said cutter being positioned adjacent to and protruding into said dispensing aperture allowing for guidance, positioning, and cutting of said floss; drive means operably mounted within said dispenser housing; a pair of rollers mounted within said dispenser housing directly above said cortically shaped discharge aperture and directly below the dispensing aperture, said pair of rollers being adapted to receive and engage said floss from said spool, said pair of rollers are operably coupled to said drive means allowing for independent rotation of each roller; and, control means for controlling and actuating said drive means for automatically dispensing a selective length of floss to be dispensed.

Figure 1:
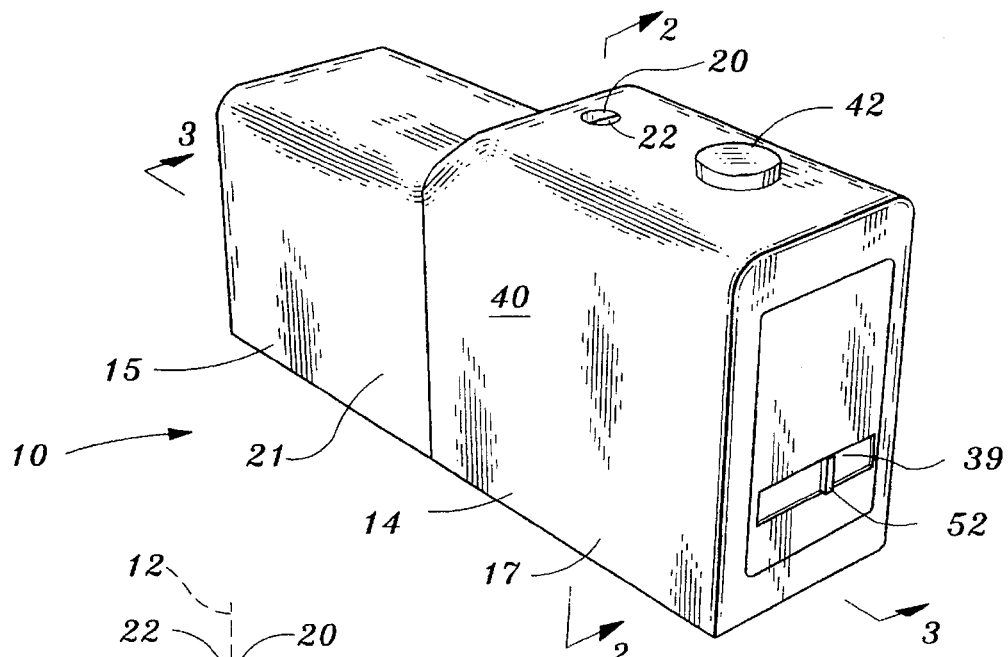
FIG. 1 shows a top perspective view of an automated floss dispensing apparatus, according to the invention.
Figure 2:
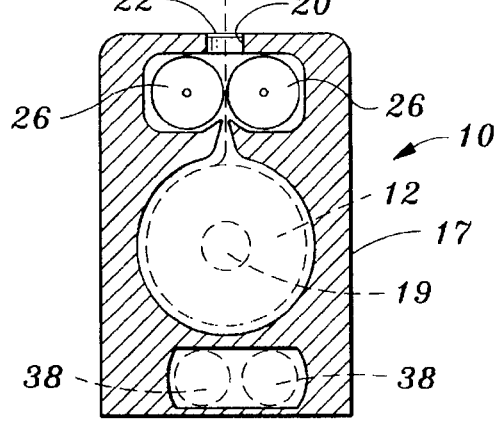
FIG. 2 shows a sectional view through 2—2 of such dispensing apparatus.
Figure 3:
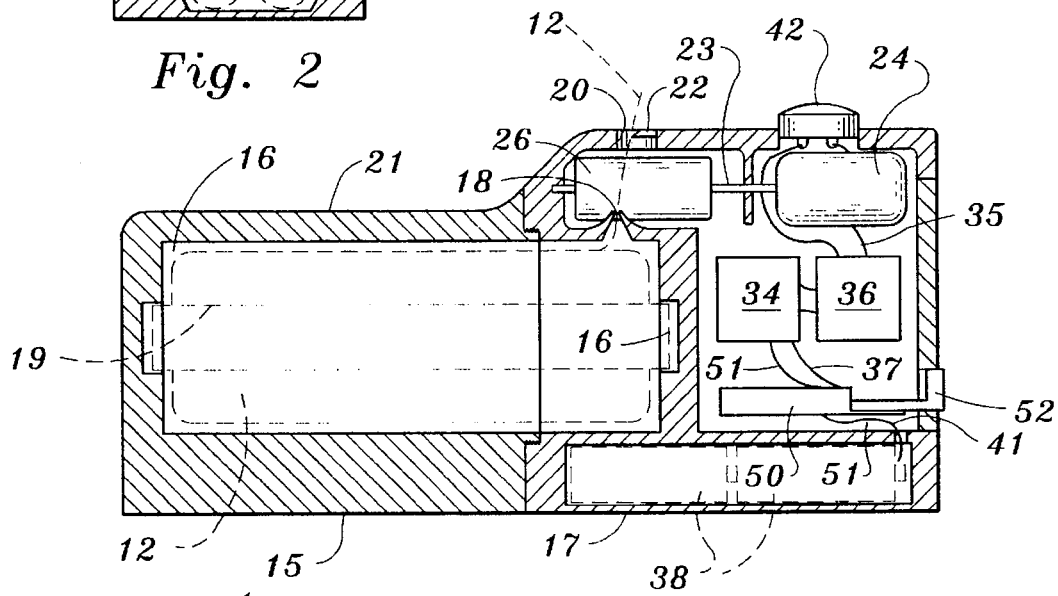
FIG. 3 shows a sectional view through 3—3 of such dispensing apparatus.
Figure 4:
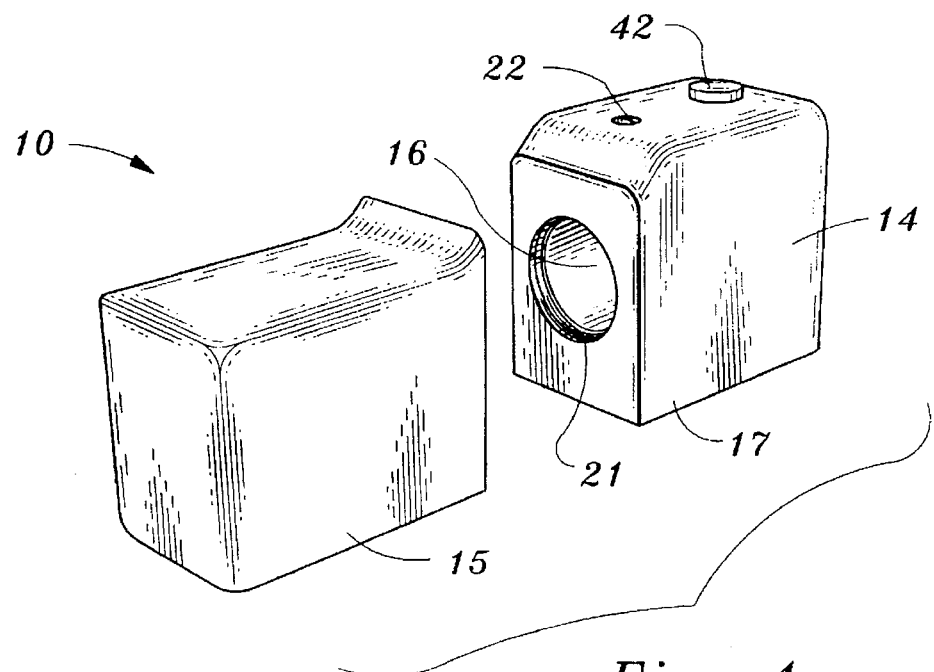
FIG. 4 shows a side perspective view of such dispensing apparatus with dispenser housing 14 separated into two units 15 and 17.

In FIGS. 1, 2, and 3 an automated dental floss dispensing apparatus 10 is shown with dental floss 12 on spool 19. Dispensing apparatus 10 preferably comprises a dispenser housing 14 comprising two units 15 and 17 having mating threads 21 for easy separation and attachment, as best seen in FIG. 4. Housing 14 is preferably composed of a durable resilient material such as plastic. Dispenser housing 14 also includes a removable front panel 39 providing for easy access to the interior of housing 14 and a non-skid grip bottom element 62, preferably composed of rubber, plastic, or other durable resilient material. A dispensing receptacle 16, shown in FIG. 3 adapted for spool 19 of dental floss 12, is configured to receive and rotatably secure a spool of floss, or alternatively, may be fashioned to secure and hold a container of sulcular cord, articulating paper, tape, strip-like material or the like. Dispensing receptacle 16 has an discharge aperture 18 through which dental floss 12, or the like, exits receptacle 16 and is fed between a pair of rollers 26 and through a dispensing aperture 20 in dispensing housing 14. Discharge aperture 18 is preferably conically shaped, best seen in FIGS. 2, 3, and 7, and has inwardly slanting walls 60 so that the floss can be easily fed and guided through the aperture preventing knotting, clumping, and misfeeding of the floss. Of course, other shaped discharge apertures may be substituted for conical shaped discharge aperture 18 albeit with inferior results because of the inherent limpness of dental floss and sulcular retraction cord which necessitates accurate control and guidance during dispensing.

Figure 7:
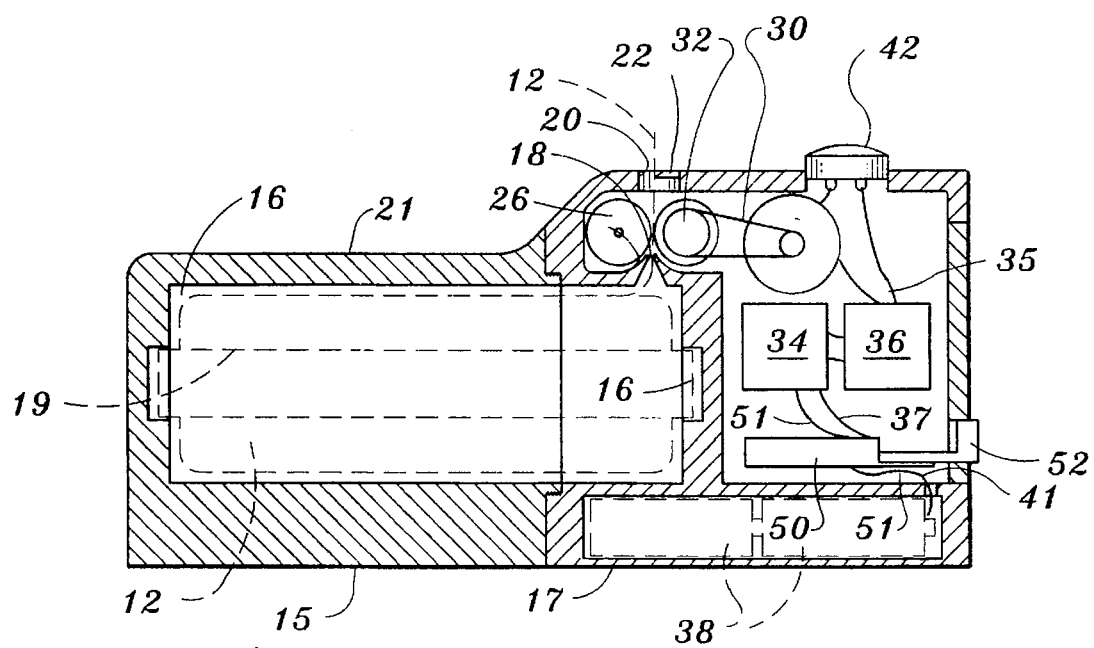
FIG. 7 shows an automated dispensing apparatus according to another embodiment of the invention.

As shown in FIGS. 2 and 3, a cutter 22 is shown disposed adjacent to dispensing aperture 20 in dispenser housing 14. Cutter 22 is preferably a sharpened blade for severing floss 12 from spool 19, and may be configured in a wide variety of ways so as to conform to different housings and dispensing applications. Drive means for driving rollers 26 preferably comprise a motor 24 powered by one or more batteries 38 operably connected by linkage 41 to motor 24. Rollers 26 are preferably mounted within dispenser housing 14 in a parallel orientation as shown in FIG. 2 and floss 12 frictionally engages with rollers 26 and is pulled from spool 19 when rollers 26 rotate. Rollers 26 are operably coupled to motor 24 by drive 23. Alternatively, rollers 26 may be coupled to motor 24 by meshing with known mechanical drive means such as a capstan 28 driven by belt 30 which is rotated by gear 32 powered by motor 24 as shown in FIG. 7, or other conventional coupling linkages well known in the art.

Rollers 26 are preferably composed of smooth silicon rollers or roller coated with silicon to facilitate smooth, even, and controllable dispensing of the floss. However, other coatings and compositions of such rollers, such as metal, Teflon, plastic, or the like, may be used, however, with inferior results.

Referring to FIG. 3, control means for controlling and actuating motor 24 for automatically dispensing a selective length of floss preferably comprises a first circuit 34 operably coupled to motor 24 and control panel 39 by linkage 35 and calibrated to control motor speed through control panel 39 on wall 40 of dispenser housing 14, and a second circuit 36 operably coupled to motor 24 and control panel 39 by linkage 37 for controlling the length of floss to be dispensed by pre-set selective activation and deactivation of motor 24 also operably linked to control panel 39. Thus, circuit 36 acts as a time delay relay or timer type circuit. Circuits 34 and 36 are pre-set and coordinated with switches 52 on control panel 39 to customize the length of floss dispensed with activation of a particular switch on panel 39. A third circuit 50 acting as a current regulator may be incorporated by linking circuit 50 by linkage 51 to batteries 38 and control panel 39 to keep current supplied to motor 24 from batteries 38 consistent, thereby assuring efficient operation of apparatus 10. Start button 42 is operably linked to motor 24 and to circuits 34 and 36. However, various sensing mechanisms well known in the art, such as "electric eyes" or sound sensors may be substituted for start button 42 if a no touch type start mechanism is desired.

Figure 5:
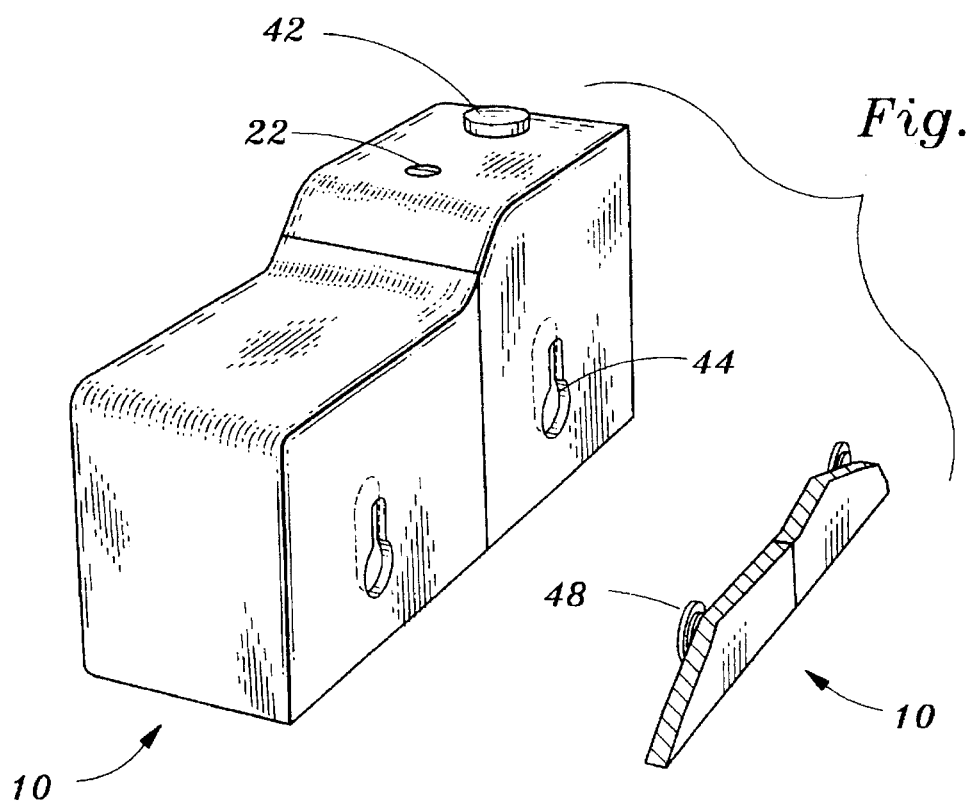
FIG. 5 shows a side view of such dispensing apparatus having slots 44 for combining with projections 48 on a different dispensing apparatus illustrating means to operably couple two or more automated dental floss dispensing apparatus units together.
Figure 6:
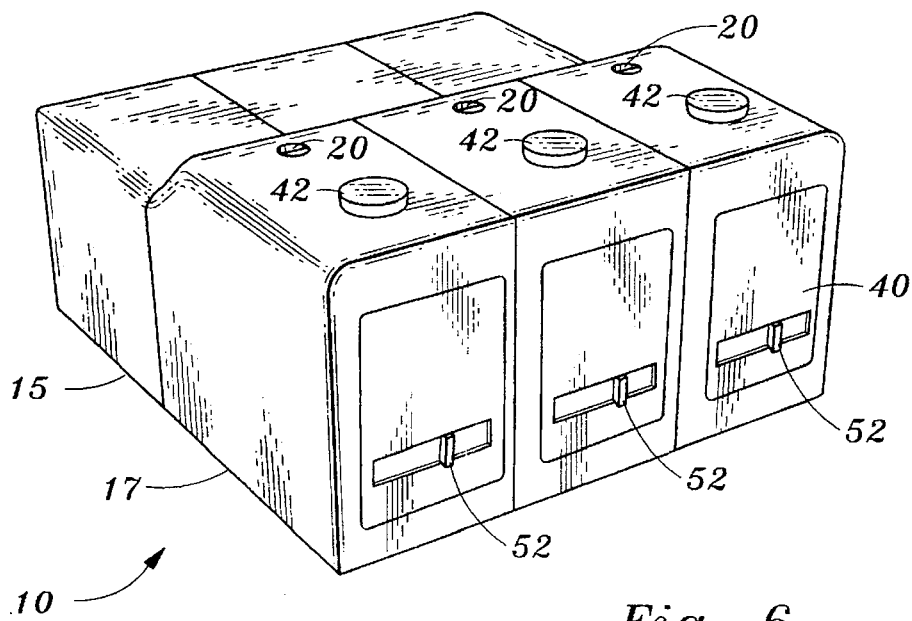
FIG. 6 shows an assembly of three automated dispensing apparatuses linked together, according to the invention.

Referring now to FIG. 5, means to operably couple two or more automated dispensing apparatuses together is provided, in one embodiment, by slots 44 adapted to secure and receive corresponding projections 48 of a different dispensing apparatus. FIG. 6 shows three such apparatuses linked together which may be a convenient and useful arrangement for a typical medical or dental office. In such combination, for example, one dispensing apparatus could be loaded with dental floss, another with retraction cord, another with tape, etc.

In alternative embodiments and applications, such as in FIG. 7 apparatus 10 may be used for sulcular cord, tape, strip-like material, or the like. In such applications dispensing apparatus 10 comprises portable dispenser housing 14 having two separable units 15, and 17 and includes a dispensing receptacle 16 adapted to receive the floss, sulcular cord, tape, or strip-like material. Dispensing receptacle has discharge aperture 18 and dispenser housing has dispensing aperture 20 with cutter 22 disposed proximate to dispensing aperture for cutting a selected length of material. Drive means are provided by motor 24 which is preferably powered by batteries 38. Motor 24 drives rollers 26 secured within dispenser housing 14. Motor 24 may be operably coupled to rollers 26 by mechanical drives well known in the art, such as a drive shaft with linkages and gear from motor 24 to roller 26. Rollers 26 are aligned with discharge aperture 18 and dispensing aperture 20 so that the floss, sulcular cord, tape, etc. passes through discharge aperture 18, between rollers 26 and out dispensing aperture 20 where cutter 22 then severs a selected length of material. Control means for controlling and actuating motor 24 preferably comprise, in this embodiment, a stepper motor or a sensor operably coupled to motor 24 to monitor and control the length of material to be dispensed and operably calibrated to dispense a selected length of material by rotation of rollers 26 by the motor shaft.

In operation and use the control mechanism may be designed to customize the dispensing apparatus 10 for a particular dispensing regimen, for example, sterile and controlled dental floss or sulcular cord dispensing in a dental office. Multiple units may be linked together and conveniently provide a sterile, controllable, and easy to use dispensing assembly.

Dispensing apparatus 10 is inexpensive and simple to manufacture, repair, and load with material to be dispensed. For example, to load dispensing apparatus 10 with a spool of dental floss the user simply separates unit 15 and 17 by unscrewing thread 21 and places spool 19 of dental floss 12 in receptacle 16. Floss 12 is then fed through discharge aperture 18 and between rollers 26 and out through dispensing aperture 20. Dispensing apparatus 10 is portable in size, automatic, and requires minimal instruction for safe, efficient, and reliable use.

Additional advantages and modifications will readily occur to those skilled in the art. The invention in its broader aspects is, therefore, not limited to the specific examples shown and described. For example, skilled artisans will be readily able to change the dimensions and shapes of the various embodiments. Alternative materials may be used for the dispenser housing such as plastic, metal, fiberglass, and synthetic polymers, and the housing designed to include a mounting bracket for wall mounted units. Housing units 15 and 17 could, alternatively, be attached together by screws, a latch, precision slip-fitted, or a side opening provided in housing 14. Various length adjustment switches may be substituted for switch 52, such as a sliding switch, swing arm switches, a rotating switch, or separate buttons for controlling the length of material to be dispensed. Cutter 22 may be provided as a stationary or automated cutter, and the dispensing opening could be located in different embodiments on the end, side, or bottom of housing 14. Similarly, start button 42 may alternatively be photosensitive, sound activated, a combination length adjustment switch having both length and start functions and activated by one button, a series of pressure sensitive buttons for different lengths material to be dispensed, or a sealed button so surface disinfection is facilitated. Alternatively, the dispensing apparatus 10 could be made eliminating the length adjustment mechanism altogether so that a set length is provided by activation of switch 52 or button 42, and if longer lengths of material are desired, the user could simple press again on the switch or continue to hold the button down. Batteries 38 may be substituted by a single battery or other power sources well known in the art. Rollers 26 may both be driven by motor 24, or alternatively one roller could be driven by motor 24 while the other roller is left idle. Accordingly, departures may be made from such details without departing from the spirit or scope of the applicant's general inventive concept.

What is claimed is:

1. An automated dental floss dispensing apparatus for dispensing waxed or unwaxed dental floss from a source of material, comprising:

a dispenser housing having a spool receptacle for enclosing and retaining a spool of floss, said spool receptacle having a conically shaped discharge aperture having inwardly slanted walls allowing said dental floss to be fed and guided through said conically shaped discharge aperture; said dispenser housing includes a dispensing aperture for dispensing said floss;

a cutter disposed adjacent to said dispensing aperture, said cutter being positioned adjacent to and protruding into said dispensing aperture allowing for guidance, positioning, and cutting of said floss;

drive means operably mounted within said dispenser housing;

a pair of rollers mounted within said dispenser housing directly above said conically shaped discharge aperture and directly below the dispensing aperture; said pair of rollers receive and engage said floss from said spool; the pair of rollers are operably coupled to said drive means allowing each roller to rotate independently of each other, and;

control means for controlling and actuating said drive means for automatically dispensing a selected length of the floss to be dispensed.

2. The automated dental floss dispensing apparatus of claim 1 wherein said pair of rollers are silicon coated, allowing for smooth and even dispensing of dental floss.

3. The automated dental floss dispensing apparatus of claim 1 wherein said dispenser housing comprises two units operably linked together.

4. The automated dental floss dispensing apparatus of claim 1 wherein said dispenser housing further includes a control panel on a wall of said dispenser, said control panel being operably coupled to said control means for controlling and actuating said drive means.

5. The automated dental floss dispensing apparatus of claim 1 wherein said drive means comprises a motor.

6. The automated dental floss dispensing apparatus of claim 5 wherein said drive means comprises a first circuit operably coupled to a motor to control motor speed and a second circuit operably coupled to said motor to control a length of floss to be dispensed by selective activation and deactivation of said motor.

7. The automated dental floss dispensing apparatus of claim 6 wherein said motor is powered by one or more batteries.

8. The automated dental floss dispensing apparatus of claim 1 further including a circuit operably coupled to said control means and to a battery means for regulating current to said drive means.

9. The automated dispensing apparatus of claim 1 wherein said dispenser housing includes a wall having a start button operably coupled to said control means.

10. The automated dental floss dispensing apparatus of claim 1 wherein said dispenser housing further includes one or more receiving slots on a wall of said dispenser housing for attachment with one or more projections on a corresponding wall of a different dispenser unit.

11. A dispensing apparatus for dispensing dental floss, comprising:

a portable dispenser housing having a dispensing receptacle with a conically shaped discharge aperture allowing for dental floss to be fed and guided through said conically shaped discharge aperture; said dispenser housing includes a dispensing aperture with a cutter disposed proximate to said dispensing aperture for cutting a selected length of material; said cutter being positioned adjacent to and protruding into said dispensing aperture allowing for guidance, positioning, and cutting of said floss;

drive means operably mounted within said dispenser housing, and a pair of rollers operably secured within said dispenser housing and positioned above said conically shaped discharge aperture and below said dispensing aperture, said pair of rollers holding and engaging floss to be dispensed; the pair of rollers being operably coupled to said drive means.

12. The dispensing apparatus of claim 11 wherein said dispenser housing comprises two units operably linked together.

13. The dispensing apparatus of claim 11 wherein said dispenser housing further includes a control panel on a wall of said dispenser, said control panel being operably coupled to said control means for controlling and activating said drive means.

14. The dispensing apparatus of claim 11 wherein said drive means comprises a motor.

15. The dispensing apparatus of claim 11 wherein said pair of rollers are coated with a layer of silicon allowing for smooth and even dispensing of a selected length of dental floss.

16. The dispensing apparatus of claim 11 wherein said dispenser housing further includes one or more receiving slots on a wall of said dispenser housing for attachment with one or more projections on a corresponding wall of a different dispenser unit.

* * * * *